United States Patent
Phipps et al.

Patent Number: 6,049,733
Date of Patent: *Apr. 11, 2000

[54] ELECTROTRANSPORT SYSTEM WITH ION EXCHANGE MATERIAL COMPETITIVE ION CAPTURE

[75] Inventors: J. Bradley Phipps, Maple Grove, Minn.; Lyn C. Moodie, Westbury, N.Y.; J. Richard Gyory, San Jose; Felix Theeuwes, Los Altos Hills, both of Calif.

[73] Assignee: ALZA Corporation, Mountain View, Calif.

[*] Notice: This patent is subject to a terminal disclaimer.

[21] Appl. No.: 08/938,769

[22] Filed: Sep. 26, 1997

Related U.S. Application Data

[63] Continuation of application No. 08/418,966, Apr. 6, 1995, abandoned, which is a continuation of application No. 08/224,766, Apr. 8, 1994, abandoned.

[51] Int. Cl.[7] ................................................ A61N 1/30
[52] U.S. Cl. ........................ 604/20; 607/149; 424/449
[58] Field of Search .................... 604/20–21, 890.1; 607/115, 149, 152–153; 424/449

[56] References Cited

U.S. PATENT DOCUMENTS

| | | |
|---|---|---|
| 4,585,652 | 4/1986 | Miller et al. . |
| 4,722,726 | 2/1988 | Sanderson et al. . |
| 4,731,049 | 3/1988 | Parsi .................................................. 604/20 |
| 4,744,787 | 5/1988 | Phipps et al. . |
| 4,747,819 | 5/1988 | Phipps et al. . |
| 4,752,285 | 6/1988 | Patelenz et al. ............................ 604/20 |
| 4,915,685 | 4/1990 | Petelenz et al. . |
| 4,927,408 | 5/1990 | Haak et al. . |
| 4,973,303 | 11/1990 | Johnson et al. . |
| 5,057,072 | 10/1991 | Phipps . |
| 5,084,006 | 1/1992 | Lew et al. . |
| 5,084,008 | 1/1992 | Phipps . |
| 5,135,477 | 8/1992 | Untereker et al. . |
| 5,147,297 | 9/1992 | Myers et al. . |
| 5,169,383 | 12/1992 | Gyory et al. ............................... 604/20 |
| 5,395,310 | 3/1995 | Untereker et al. ........................ 604/20 |
| 5,871,460 | 2/1999 | Phipps et al. . |

FOREIGN PATENT DOCUMENTS

| | | |
|---|---|---|
| 0182520 | 5/1986 | European Pat. Off. ......... A61N 1/30 |
| 0318776 | 6/1989 | European Pat. Off. ......... A61N 1/30 |
| 410009 | 5/1934 | United Kingdom . |
| 9115260 | 10/1991 | WIPO . |
| 9116943 | 11/1991 | WIPO . |
| WO 9204938 | 4/1992 | WIPO .............................. A61N 1/30 |

*Primary Examiner*—Mark Bockelman
*Attorney, Agent, or Firm*—Owen J. Bates; D. Byron Miller; Steven F. Stone

[57] ABSTRACT

An electrotransport apparatus using dispersed ion exchange material (19,83) is disclosed. The ion exchange material (19,83) may be dispersed in either the donor electrode assembly (10), the counter electrode assembly (10) or both electrode assemblies. The dispersed ion exchange material (83) comprises mobile ionic species (84-2) and substantially immobile ionic species (P). The dispersed ion exchange material (83, 84-2) interacts with competitive species (86) generated during electrotransport to render those species substantially immobile (87). Electrotransport devices exhibiting reduced polarization are also disclosed.

30 Claims, 1 Drawing Sheet

ELECTROTRANSPORT SYSTEM WITH ION EXCHANGE MATERIAL COMPETITIVE ION CAPTURE

This application is a continuation of U.S. patent application Ser. No. 08/418,966 filed Apr. 6, 1995, now abandoned which is a continuation of U.S. patent application Ser. No. 08/224,766 filed Apr. 8, 1994, now abandoned.

TECHNICAL FIELD

This invention generally concerns apparatuses for the electrically assisted delivery of therapeutic agent through a body surface such as skin or a mucosal membrane. Such apparatuses are referred to broadly herein as electrotransport devices.

More specifically, this invention relates to electrotransport drug delivery devices or systems in which active species, agents or drugs are directly or indirectly delivered through a body surface (eg, skin) of a patient by application of electromotive force.

BACKGROUND OF THE INVENTION

The present invention concerns apparatuses for transdermal delivery or transport of therapeutic agents, typically through iontophoresis. Herein the terms "electrotransport", "iontophoresis", and "iontophoretic" are used to refer to methods and apparatus for transdermal delivery of therapeutic agents, whether charged or uncharged, by means of an applied electromotive force to an agent-containing reservoir. The particular therapeutic agent to be delivered may be completely charged (ie, 100% ionized), completely uncharged, or partly charged and partly uncharged. The therapeutic agent or species may be delivered by electromigration, electroosmosis or a combination of the two. Electroosmosis has also been referred to as electrohydrokinesis, electro-convection, and electrically-induced osmosis. In general, electroosmosis of a therapeutic species into a tissue results from the migration of solvent, in which the species is contained, as a result of the application of electromotive force to the therapeutic species reservoir, ie, solvent flow induced by electromigration of other ionic species. Thus, as used herein, the terms "iontophoresis" and "iontophoretic" refer to (1) the delivery of charged drugs or agents by electromigration, (2) the delivery of uncharged drugs or agents by the process of electroosmosis, (3) the delivery of charged drugs or agents by the combined processes of electromigration and electroosmosis, and/or (4) the delivery of a mixture of charged and uncharged drugs or agents by the combined processes of electromigration and electroosmosis.

During the electrotransport process certain modifications or alterations of the skin may occur such as increased ionic content, hydration, dielectric breakdown, extraction of endogenous substances and electroporation. Any electrically assisted transport of species enhanced by modifications or alterations to a body surface (eg, formation of pores in the skin) are also included in the term electrotransport as used herein.

Iontophoretic devices for delivering ionized drugs through the skin have been known since the 1800's. Deutsch United Kingdom Patent No. 410,009 (1934) describes an iontophoretic device which overcame one of the disadvantages of such early devices, namely, that the patient needed to be immobilized near a source of electric current. The Deutsch device was powered by a galvanic cell formed from the electrodes and the material containing the drug to be transdermally delivered. The galvanic cell produced the current necessary for iontophoretically delivering the drug. This device allowed the patient to move around during iontophoretic drug delivery and thus required substantially less interference with the patient's daily activities.

In present iontophoresis devices, at least two electrodes are used. Both of these electrodes are disposed so as to be in intimate electrical contact with some portion of the skin of the body. One electrode, called the active or donor electrode, is the electrode from which the ionic substance, agent, medicament, drug precursor or drug is delivered into the body via the skin by iontophoresis. The other electrode, called the counter or return electrode, serves to close the electrical circuit through the body. In conjunction with the patient's skin contacted by the electrodes, the circuit is completed by connection of the electrodes to a source of electrical energy, eg, a battery; and usually to circuitry capable of controlling current passing through the device. For example, if the ionic substance to be driven into the body is positively charged, then the positive electrode (the anode) will be the active electrode and the negative electrode (the cathode) will serve to complete the circuit. If the ionic substance to be delivered is negatively charged, then the cathodic electrode will be the active electrode and the anodic electrode will be the counter electrode.

Furthermore, existing iontophoresis devices generally require a reservoir or source of the beneficial agent or drug, preferably an ionized or ionizable species (or a precursor of such species) which is to be iontophoretically delivered or introduced into the body. Such drug reservoirs are connected to the anode or the cathode of an iontophoresis device to provide a fixed or renewable source of one or more desired species or agents.

Perhaps the most common use of iontophoresis today is in diagnosing cystic fibrosis by delivering pilocarpine transdermally. Iontophoretically delivered pilocarpine stimulates sweat production, the sweat is collected, and is analyzed for its chloride ion content. Chloride ion concentration in excess of certain limits suggests the possible presence of the disease.

Thus an electrotransport device or system, with its donor and counter electrodes, may be thought of as an electrochemical cell having two electrodes, each electrode having an associated half cell reaction, between which electrical current flows. Electrical current flowing though the electronically conductive (eg, metal) portions of the circuit is carried by electrons (electronic conduction), while current flowing through the liquid-containing portions of the device (ie, the drug reservoir in the donor electrode, the electrolyte reservoir in the counter electrode, and the patient's body) is carried by ions (ionic conduction). Current is transferred from the metal portions to the liquid phase by means of oxidation and reduction charge transfer reactions which typically occur at the interface between the metal portion (eg, a metal electrode) and the liquid phase (eg, the drug solution). A detailed description of the electrochemical oxidation and reduction charge transfer reactions of the type involved in electrically assisted drug transport can be found in electrochemistry texts such as J. S. Newman, *Electrochemical Systems* (Prentice Hall, 1973) and A. J. Bard and L. R. Faulkner, *Electrochemical Methods, Fundamentals and Applications* (John Wiley & Sons, 1980).

As electrical current flows, oxidation and reduction of a chemical species takes place. A variety of electrochemical reactions can be utilized, and these generally fall into two major classes. In one major class, the electrochemical reaction results in the generation of a mobile ionic species with a charge state (ie, + or −) like that of the drug in its ionic form. Such a mobile ionic species is referred to as a "competitive species" or a "competitive ion" because the species competes with the drug for delivery by electrotransport. Exemplifying this class of reactions is what is referred to in the art as a "sacrificial" reaction where electrode material is consumed in the reaction with generation of a competitive ion. A further example of this first major class of electrochemical reactions is a de-intercalation reaction where a competitive ion is expelled from the electrode. A third example of this first major class of electrodes is the common situation where a competitive ion is generated by oxidation or reduction of a substance in contact with the electrode. Reactions falling in the first major class may be either anodic or cathodic.

Examples of anodic reactions where a competitive cation is generated include:

$$M^0 \rightarrow M^{z+} + Ze^- \tag{1}$$

where $M^0$ is a metal which is oxidized to the +Z state and $M^{z+}$ is the competitive ion;

$$M_xWO_3 \rightarrow M_{x-1}WO_3 + M^+ + e^- \tag{2}$$

where $M^+$ is the competitive ion, and $$H_2Q \rightarrow Q^0 + 2H^+ + 2e^- \tag{3}$$

where $Q^0$ is a species which is stable in its reduced state and $H^+$ is the competitive ion.

Examples of cathodic reactions where a competitive anion is generated include:

$$AgCl + e^- \rightarrow Ag^0 + Cl^-. \tag{4}$$

$$C_nFeCl_3 + e^- \rightarrow C_nFeCl_2 + Cl^- \tag{5}$$

and $$Cl_2 + 2e^- \rightarrow 2Cl^- \tag{6}$$

where $Cl^-$ is the competitive anionic species in each of reactions, 4, 5, and 6.

In a second major class of electrochemical reactions, no competitive ion is generated during the operation of the system. In one example of this class of reactions, the species to be reduced or oxidized exist in solution and the charge transfer oxidation or reduction reaction is catalyzed at the electrode surface. The products of the reaction are gaseous or soluble in the reservoir and either are neutral or exist in a charge state opposite that of the drug in its ionic form. A reaction product having a charge state opposite that of the drug to be delivered would not be "competitive" as the term is used here. Example of anodic reactions of this latter class which do not generate a competitive ion include:

$$Fe(CN)_6^{4-} \rightarrow Fe(CN)_6^{3-} + e^- \tag{7}$$

$$C_nFeCl_2 + Cl^- \rightarrow C_nFeCl_3 + e^-. \tag{8}$$

Examples of cathodic reactions which do not generate a competitive ion include:

$$M^{z+} + ze^- \rightarrow M^o \tag{9}$$

$$M_{x-1}WO_3 + M^+ + e^- \rightarrow M_xWO_3 \tag{10}$$

$$Q^0 + 2H^+ + 2e^- \rightarrow H_2Q, \tag{11}$$

and $$Fe^{3+} + e^- \rightarrow Fe^{2+} \tag{12}$$

Reactions 7, 9, 11, and 12 are catalyzed by an appropriately polarized surface of a substantially inert or catalytic electrode, such as the surface of a catalytic electrode comprising carbon, gold, stainless steel or platinum. Reactions 8 and 10 are intercalation/insertion reactions where an ionic species is incorporated into the electrode material during operation of the device.

It is particularly important in attempting to determine which of the above major classes a particular system falls into, to focus upon the species generated during the electrochemical reaction(s) as it (or they) relate to the drug or agent to be delivered. In particular, the focus should be whether the species generated will electromigrate in the same direction (eg, toward the skin) as the drug or agent of choice under the influence of the electric potential gradient. In other words, it is significant that an ionic species is being produced only in so far as ionic species competes with a drug or agent to be delivered and thereby adversely impacts biocompatability of the electrotransport system (eg, where the competing ionic species produced is not biocompatible), drug stability, or drug delivery efficiency.

In the prior art, iontophoresis electrodes employing the first approach, above, have usually included current distributing members or structures referred to as "active" or "electroactive" or "electrochemically reactive" in the sense that their chemical compositions were materially altered during the agent delivery process. For example, sacrificial current distributing members which were oxidized or reduced themselves have been discussed. Use of sacrificial current distribution members can avoid the adverse effects associated with utilization of catalytic current distributing members (eg, pH changes). Electrodes with sacrificial current distributing members are disclosed in U.S. Pat. No. 4,744,787 to Phipps, et al and U.S. Pat. No. 5,135,477 to Untereker, et al. Intercalation electrodes are discussed in patents issued to those same inventors.

The current distributing member in an iontophoresis electrode employing the second approach, above, have usually been constructed to include substantially inert materials such as stainless steel or platinum. "Inert" as that term is used in the art normally means that the material is catalytic, ie, it catalyzes an oxidation or reduction reaction by providing or accepting electrons to or from other chemical species but does not itself take part in the reaction by being chemically or physically altered. The material of the electrode structure, eg, the current distributing member, therefore is "inert" only in the sense of itself not being chemically altered in the reduction or oxidation reaction in which it participates.

When oxidation or reduction occurs at an electrode surface, ionic species must be transported to maintain electroneutrality throughout the system. Electrically-assisted transport or electrotransport is defined as the mass transport of a particular chemical species through a biological interface or membrane when an electrical potential gradient is imposed across said interface or membrane. Four physical processes contribute to this transport: passive diffusion, electromigration, electroporation, and convection. Even though drug electrotransport systems are well characterized, there is a continuing need to enhance their drug delivery efficiency. Enhanced efficiency permits smaller, less expensive and more versatile devices to be developed. Optimization of the three physical transport processes is one approach to enhance such efficiency.

In the iontophoresis art, various approaches have been taken to increase the drug delivery efficiency of (ie, the amount of drug delivered per unit of applied electrical current) transdermal drug or agent delivery. This issue was addressed in U.S. Pat. No. 5,135,477 to Untereker et al and in earlier related U.S. Pat. Nos. 4,744,787 and 4,747,819 both to Phipps et al. The above patents disclose increased electrotransport drug delivery efficiency by the selection, (in accordance with the Untereker et al patent) of: (1) the particular form of the drug to be delivered, (2) an electrochemically active component of the drug delivery apparatus, or (3) both, so that during the operation of the apparatus competitive species (i.e, ions carrying the same charge as the drug ions and thus in competition with the drug for carrying current into the body) were reduced or eliminated. The basic solution proposed by Untereker et al has the drawback in that the particular agent or drug to be iontophoretically delivered may be unavailable in a form with the desired counter ion. Even if the drug is available in the proper salt form (eg, when using a silver anodic electrode, the drug is preferably in the form of a chloride salt so that the drug counter ion is chloride), the net or overall electrochemical process ($Ag+Cl^- \rightarrow AgCl+e^-$) may require more counter ion (eg, $Cl^-$) than can be supplied by the drug salt alone. This is particularly true for highly potent or expensive drugs, where the concentration of drug salt within the reservoir is generally relatively small. Put otherwise, a particular combination of drug/drug counter ion, and electroactive component of the device to enhance efficiency of the device in accordance with the teachings of the above patents may not be practical due to limitations on the availability of drug salt in the appropriate form or the amount of drug salt that can be added to the reservoir. It is one objective of this invention to overcome these limitations by providing electrochemically appropriate ions from a source other than, or in addition to, those supplied by the drug salt so as to enhance agent or drug delivery efficiency.

Subsequent to the work of Untereker et al noted above, several patents have disclosed the use of various means to inhibit the flow of ions competitive with the species to be delivered. U.S. Pat. No. 4,722,726 to Sanderson et al discloses an iontophoresis device having an ion mobility inhibiting means (ie, a discrete layer of ion exchange membrane material) disposed between, for example, an electrode/electrolyte solution and a source of the ionic species to be delivered, ie, a drug solution. The ion exchange membranes used by Sanderson et al included the AR103-QZL membrane sold by Ionics, Inc. and Raipore 4010 and 4035 membrane sold by RAI Research Corp. A device of the Sanderson et al patent has electrodes which generate hydronium ions and hydroxyl ions during its operation. Thus, the purpose of Sanderson's ion-exchange membrane is to inhibit the passage of ions of similar charge (ie, similar to that of the drug ion) from the electrode/electrolyte solution to the drug solution where they could compete. However, Sanderson et al do not attribute any significance to the selection of the ion exchange medium counter ion. Of particular significance is the fact that the ion exchange membrane disclosed by Sanderson et al is selectively permeable to ions having a charge which is opposite the charge of the drug species to be delivered. To function properly, the ion exchange material must provide a continuous barrier to the passage of ions carrying the same charge as the drug ion.

U.S. Pat. No. 4,731,049 to Parsi discloses an iontophoresis device employing a drug reservoir in which the drug to be delivered is initially bound to an ion exchange medium or an immobilized ligand affinity medium. Ions such as hydrogen ($H^+$), sodium, potassium, hydroxyl, chloride, and sulfate ions are generated at the electrode or provided by an ion reservoir and are exchanged for the bound drug ions, thereby releasing the drug ions for delivery into the patient's body. Parsi discloses a donor electrode assembly having a hydrophilic polymer-based electrolyte reservoir and drug reservoir layers, a skin-contacting hydrogel layer, and optionally one or more semipermeable membrane layers. The ion exchange media is disclosed to be in the form of beads, powder, packed fibers, woven or knit fibers, microporous or macromolecular resin or liquid resin. Parsi employs electrodes which are electrochemically catalytic, ie, the electrodes are composed of materials (eg, carbon, graphite or metal, such as platinum group metals) which catalyze the electrochemical reaction as described above. Parsi is limited in its application to systems where drug can be bound to an ion exchange resin or medium or an immobilized ligand affinity medium, and for this reason, must possess a charge opposite that of the drug ion. U.S. Pat. No. 4,915,685 to Petelenz et al discloses a system closely related to that disclosed by Parsi.

U.S. Pat. No. 4,927,408 to Haak et al discloses an electrotransport system having a novel donor electrode pad. The pad comprises an agent reservoir, and an electrolyte reservoir separated by a selectively permeable membrane. Microporous polymers, ie, membranes, which are selectively permeable based on the size of the permeating species and ion-exchange membranes which are selectively permeable based on the charge of the permeating species, are disclosed to be useable in the electrode pad of Haak. The charge selective membranes of Haak can be selected to bind, eg, by ion-exchange or chelation, particularly interfering or undesirable species. For example, interfering metals can be removed by this expedient.

Related to the above Haak et al '408 patent is International Application No. WO91/16943 which provides substantial additional detail regarding selectively permeable membranes which are selective for the particular size or molecular weight of the diffusing species.

European Patent Application WO91/15260 (PCT/US91/02030) discloses, in one embodiment, an iontophoretic device having a two layer active electrode element. A single layer active electrode element embodiment also is disclosed. In the embodiments disclosed in the '15260 application, layers of anionic, cationic or amphoteric polymers are used. In a preferred structure, an impermeable layer is interposed between the two layers of the electrode. Enhancement of shelf life is a particular objective of the '15260 application.

U.S. Pat. No. 4,585,652 to Miller et al discloses delivery of bioactive substances using an electrode comprising a polymer which is "charged" or conductive and which can be electrochemically cycled between a charged and a neutral or insulating state. In the charged state, the polymer is located with bioactive counter ions which are delivered when the polymer is cycled to the neutral state. An example of a charged polymer is poly(vinylferrocene). Examples of conductive polymers are poly(pyrroles), substituted poly (thiophenes), and similar poly(heterocyclic) materials.

U.S. Pat. No. 5,057,072 to J. B. Phipps discloses an iontophoresis electrode which uses a current distribution member and a drug reservoir containing an ionic drug. The current distribution member is separated from the drug reservoir by a membrane or a material selective for ions having a charge opposite to the charge of the drug to be delivered. The cation or anion selective layer or coating of material is applied directly to the current distributing member and prevents the migration into the drug reservoir of ions produced during the oxidation or reduction of the current distributing member.

U.S. Pat. No. 5,084,008 to J. B. Phipps discloses an improved iontophoresis electrode having a current distribution member in direct or intimate contact with a salt layer or an ion source layer. In direct or intimate contact with the salt layer or ion source layer is a size selective membrane (ie, a semipermeable membrane) or a material which is charge selective for ions having a charge opposite to the charge of the drug to be delivered. This improved structure of the iontophoresis electrode is preferably employed using a current distributing member which is itself oxidized or reduced during the process of drug delivery.

The above patents which disclose the utilization of charge selective layers or membranes to enhance device efficiency operate on the theory of Donnan exclusion. Donnan exclusion, in the case of a charge selective membrane (eg, an ion-exchange membrane), means that the fixed charge of the membrane reduces the likelihood that ions or molecules having a similar charge from passing through the membrane due to electrostatic repulsion. The type of fixed charge, and the charge density within the ion pathways favor the passage of species having definable characteristics, ie, a charge which is opposite the fixed charge on the membrane. Utilization of the principle of Donnan exclusion, in the context of an electrotransport device having a charge selective membrane, has the drawback of tending to create polarization within the entire device or within a device component. An increase in polarization tends to increase the voltage necessary to deliver agent or ion. A voltage increase within an electrotransport device normally requires an increase in the number of batteries to operate the device and therefore an increase in device size, device complexity, device cost or a combination of these factors.

Size exclusion, in the case of a size selective membrane, means simply that the pore size of the membrane is too small to permit specific molecules or ions to pass. Physical size or molecular weight restriction prevents or hinders the passage of species through the membrane. Utilization of size selective membranes also can create polarization as discussed above if the "excluded" species tend to have the same (+/−) charge.

The present invention overcomes the problems encountered in the prior art and is not suggested or disclosed in the references alone or in combination. Moreover, utilization of the present invention tends to permit smaller, less complex and less expensive electrotransport devices to be built. In addition, the present invention allows utilization of a wider variety of salts and lower drug content than is possible with prior art devices.

DISCLOSURE OF THE INVENTION

The present invention derives from the discovery that a discrete layer, membrane, ion mobility inhibiting means or zone is not necessary to the enhancement of electrotransport drug or agent delivery. In particular, this invention relates to the incorporation of ion exchange materials which, in one aspect, provide a means of rendering competitive ions substantially immobile, and in another aspect provide a means of facilitating an electrochemical reaction where no competitive species are generated.

In one aspect, the present invention is an electrode assembly for an electrotransport delivery device comprising an electrode and at least one distributed or dispersed ion exchange material. An ion exchange material of this invention comprises mobile ionic species and substantially immobile ionic species. In one practice, the ion exchange material or ion exchange macromolecule is uniformly or homogeneously dispersed in the drug reservoir. In a less preferred practice, the ion exchange material is uniformly dispersed within an "in-line" skin contact adhesive, which adhesive is placed between the drug or salt (counter) reservoir and the patient's skin and which helps secure the reservoir to the patient. In a more preferred practice, the electrode, itself, will be a composite structure comprising an electronically conductive composition and an ion exchange material.

The mobile ionic species chosen will be of a type which interacts with a competitive species generated during operation of the electrotransport device so as to render the competitive species substantially immobile or otherwise making it substantially non-responsive to external electromotive forces. A suitable ion exchange material is generally substantially insoluble in the medium in which it is dispersed. Generally, this means the ion exchange material will be substantially insoluble in (1) the liquid solvent used to "hydrate" the reservoir matrix (most typically, the reservoir matrix is hydrated with water due to its excellent biocompatability) and (2) the polymer of the electrode, reservoir or adhesive matrix. More preferably, the ion exchange material has a minimal water soluble fraction since any low molecular weight water soluble fraction has the potential to be undesirably delivered into the patient by electrotransport. The water soluble fraction of any ion exchange material can be determined by washing the resin in water and calculating the weight loss of the material. Preferably, the ion exchange material has a water soluble fraction of less than about 0.1 wt % and most preferably less than about 0.001 wt %. The ion exchange material, while dispersed within a reservoir, may be in direct and intimate contact with an electrode or current distributing member. The ion exchange material described herein may be located essentially anywhere within ion conducting portions of the electrotransport device, provided most or all competitive ionic species generated during operation of the device interact with the mobile ionic species of the ion exchange material before they reach the skin surface of the agent recipient and thereby become immobilized. While the ion exchange material may be dispersed within any ion-conducting portion or portions of the electrotransport device, it is preferred to place the dispersed ion exchange material as far away from the patient body surface-contacting portions of the device as is possible. Thus, the ion exchange material is least preferably dispersed in a layer of skin-contacting adhesive positioned between the drug reservoir and the skin, is more preferably dispersed in the drug reservoir, and is most preferably dispersed in the current distribution elements (ie, the electrodes) of the device.

When a sacrificial electrode is chosen to deliver a positively charged drug ion, $D^+$, (and assuming all other factors such as concentration are equal), the competitive ions generated at the anode in the oxidative process, will be positively charged metal ions. The ion exchange material is chosen in view of the competitive ion(s) generated with the express intent of rendering the positively charged competitive ion(s) immobile or at least substantially non-responsive to electromotive forces or electromigration tendencies. Thus an electrode assembly of this invention, by inclusion of a dispersed ion exchange material, will effectively reduce iontophoretic delivery of oxidatively produced ions which compete with the drug or agent to be delivered. This increases the efficiency associated with delivery of the drug or other beneficial agent. It is a further advantage of this invention that the cations generated during operation of the device, particularly metal cations, may have an undesirable toxicity. Prevention of such toxic species from reaching the skin, and the attendant reduction in possible toxicity due, eg, to the presence of metal cations, is a particular advantage of this invention. A further advantage of this invention is the reduction of the drug degradation processes which metal cations sometimes cause.

In a further practice of this invention, the above ion exchange material or materials are selected to provide some other desired property to the electrode structure or component in which it is dispersed. For example, the ion exchange material may provide hydrophilicity or other desirable property to the assembly component in which it is dispersed.

In yet another practice of this invention, the ion exchange material may be uniformly dispersed or distributed throughout each of several individual ion conducting portions of the electrode assembly. This approach tends to reduce the overall electrode thickness, to reduce polarization, and enhance drug or agent delivery efficiency of this device.

The terms "immobile" or "immobilized" are used extensively herein. Those terms are to be broadly construed to mean any of the physicochemical processes or interactions which produce or generate a species which does not compete with the drug ion (or which can migrate only to a limited extent), because of size or charge state in response to an electromotive force. Specifically, and without limitation, the physicochemical processes or "interactions" intended by this terminology include deposition, precipitation, neutralization, intercalation, association, complexation or chelation. The net effect of the interaction, "capture", or "binding" process is to render the competitive species substantially immobile. This interaction can occur within or in the vicinity of the ion exchange material or the ion exchange material may provide a source of mobile species which interact with the competitive species outside or far from the ion exchange material, as long as the competitive species generated is essentially prevented from migrating into the body surface. While irreversible interactions are preferred, reversible interactions may also be adequate provided that the mobility or concentrations of the reversibly-held, unwanted, competitive species is reduced substantially below the mobility or concentration of the agent to be delivered. Preferably, the transport number of the competitive species is less than 50%, more preferably less than 1%, of the transport number of the active agent being delivered when the device of the present invention is in operation.

The term "ion exchange material" is used extensively herein. This term is also to be broadly construed to mean essentially any material comprising mobile ionic species and substantially immobile ionic species where the immobile ionic species has the same charge state as the drug or agent but has sufficient mass, size, or molecular weight so as to reduce substantially its mobility in response to an applied electromotive force. It is to be understood, however, that most species will have at least some mobility in response to electromotive forces. Other terms used to describe the immobile ionic species which comprises a part of the ion exchange material include polymer, copolymer, oligomer, ionomer, polyelectrolyte, resin, colloid, micelle, particle and the like. An ion exchange material of this invention may be synthetic or natural.

While the ion exchange material used herein will generally be primarily organic in composition (ie, hydrocarbon-based) it is within the contemplation of this invention that the ion exchange material may be primarily inorganic in composition (eg, a ceramic composition). Generally speaking, the immobile ionic species will have a number average molecular weight in the range of at least about ten times greater than the molecular weight of the drug or agent to be delivered by electrotransport. A preferred polymeric immobile ionic species would be crosslinked and thereby rendered substantially insoluble in water.

Much of the above discussion relates to the class of electrochemical reactions where competitive ionic species are generated. As is noted above, there is a second class of reactions where no competitive ionic species are generated. In this later class of reactions, the dispersed ion exchange material will provide at least one of the reactants. By providing reactant (in part or in their entirety) the ion exchange material enhances the likelihood of occurrence of the reaction (or reactions) where no competitive ions are generated. Illustrating this, to facilitate electrotransport of an anionic drug $D^-$, the ion exchange material would provide a mobile cation which is reduced at the cathode as is suggested by reactions 9 and 12, above. These reduction reactions would be catalyzed at the surface of the cathode.

In the case where the cathode is an intercalation material (eg, $M_{x-1}WO_3$ or conductive polymers like those suggested by Miller et al U.S. Pat. No. 4,585,652), then the ion exchange material would provide ionic species capable of participating in the intercalation reaction. For example, if the cathode were sodium tungstate in a partially oxidized state, then the ion exchange material would provide a source of sodium ion or other cation capable of being intercalated into the cathode structure during operation of the device, as indicated by reaction 10 above.

As a third example, the ion exchange material may provide an ionic species, opposite in charge state to the drug in its ionic form, which is not reduced at the cathode nor intercalated into the cathode, but instead is a reactant critical to the formation of a noncompetitive product. This type of scenario is suggested by reaction 11 above. In this case, the ion exchange material is a source of hydronium ion, $H_3O^+$. Ion exchange materials with mobile hydronium ions have been employed in the prior art as buffering agents (eg, Sanderson U.S. Pat. No. 4,722,726 to counteract the effect on reservoir pH due to generation of hydroxyl ion at the cathode (eg, via the reaction $H_2O+e^- \rightarrow \frac{1}{2}H_2+OH^-$). In contrast, this example of the invention utilizes an ion exchange material as a source of hydronium ion which facilitates the formation of a noncompetitive species (eg, $H_3O^+ + OH^- \rightarrow H_2O$).

The above examples of this invention have focused on anodic and cathodic reactions. Anodic reactions were selected to illustrate the use of on exchange materials for the "capture" of competitive ions generated at the node. Cathodic reactions were used to illustrate the use of ion exchange materials for the "facilitation" of reactions, which generate no competitive ions. This was done to simplify the discussion and is not intended to restrict the use of ion exchange materials for one purpose or the other to a particular type of electrode, ie, anode or cathode. Ion exchange materials can be used for either purpose at either electrode, as appropriate for the particular drug to be delivered. In addition, the principles illustrated above can be used in conjunction with the counter electrode of the device to prevent generation or delivery of toxic or otherwise "unwanted" species into or out of the counter electrode reservoir whether or not such species are "competitive" as the term is used herein.

A "composite electrode structure", "composite drug reservoir", "composite electrode" or "composite material" as those terms are used herein mean that the reservoir, electrode, material or structure comprises at least two physically or chemically distinct phases. The ion exchange material comprises one phase which would be dispersed within one or more other materials or phases. Because the ion exchange material is dispersed within the composite structure in accordance with this invention (ie, there is no discrete layer, membrane or highly-concentrated zone of ion exchange material), ion migration is not required to occur through the ion exchange material. In a preferred practice, the ion exchange material is commingled with the electroactive substance thereby generating a composite electrode structure, or less preferably is commingled with the drug substance within the drug reservoir thereby generating a "composite" drug reservoir structure.

Put another way, an ion exchange material of this invention is not present as a discrete or continuous structure (eg, a membrane or layer), which separates one component of the device from another. Instead, the ion exchange material is distributed, within and throughout the electrode, the drug reservoir, the skin adhesive or other structure (or each structure) of the electrotransport system. Generally speaking, dispersed ion exchange materials are particulate, having a major dimension in the range of about 0.1 to 1200 microns. Particle sizes in the upper half of this range (eg, about 600 to 1200 microns) are preferred from the standpoint of optimizing electrotransport drug flux. Particle sizes at the lower end of this range (eg, about 1 to 600 microns and most preferably in the range of about 5 to 150 microns) are preferred from the standpoint of ease of processing and manufacturability. The ion exchange material, to be effective, must be in a drug or agent-transmitting relationship in the system. This means the material, regardless of where it is located, must be able to interact with the drug or agent flux during electrotransport.

The term "distributed" as used herein is not necessarily intended to mean "uniformly distributed", within the device structure. The term "distributed" means that the ion exchange material is sufficiently dispersed, whether particles, grains, pellets, colloids, or micelles, so that ionic polarization due to size selectivity or charge selectivity within the operant portion of the device, is substantially avoided.

DETAILED DESCRIPTION OF THE INVENTION

Figure 1:
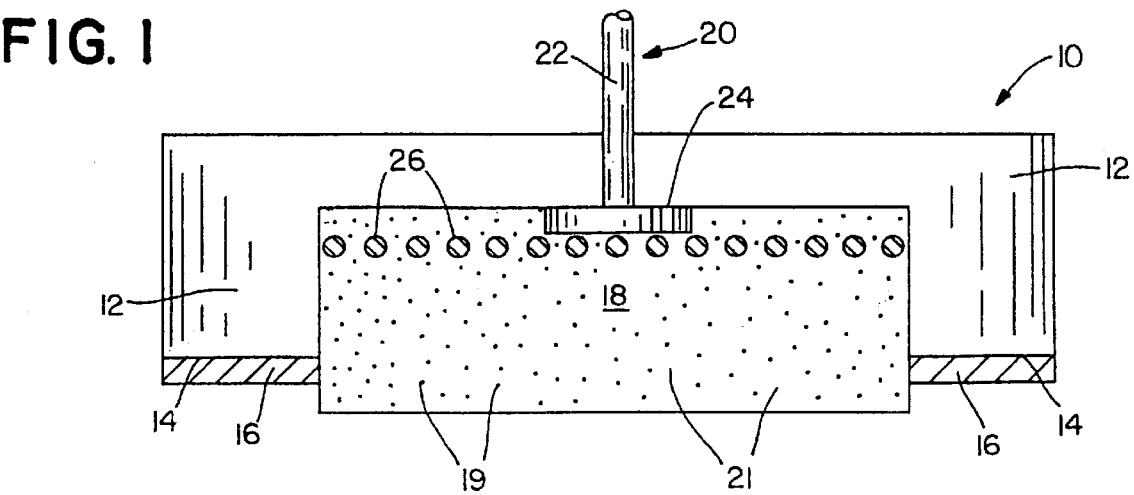
FIG. 1 is a cross-sectional view of an electrotransport electrode according to the present invention.

Reference is now made to FIG. 1 included herewith. In the FIG. 1, there is depicted, schematically, in cross section, a single, substantially circular donor electrode assembly 10 which is intended for use in an iontophoretic drug delivery device. It is to be understood that electrode assembly 10 is but one of the two electrode assemblies necessary for operation of a device and that a necessary source of electrical energy, eg, a battery, also is not shown.

Electrode assembly 10 comprises an insulative support or housing which, in cross section, is generally "U" shaped and which preferably is flexible. In a preferred embodiment, support 12 is produced from a self-supporting, non-conductive polymeric foam. In this embodiment, perimeter surface 14 of housing 12 optionally has disposed thereon a skin-compatible, pressure-sensitive biomedical adhesive 16 which holds electrode assembly 10 in place on the patient's skin during iontophoretic drug delivery. Electrode assembly 10 may be held in place by other means, eg, a strap (not shown), or in certain cases matrix 21 (discussed below) is itself sufficiently adhesive to adhere electrode assembly 10 to the skin, in which instances adhesive 16 would not be needed. In the instance where matrix 21 is sufficiently adhesive, ion exchange material could be dispersed within matrix 21. Under these circumstances, the ion exchange material would be in a drug or agent transmitting relationship with respect to a patent, as that term is used herein. In this embodiment, a periphery adhesive could be omitted or redundant.

Electrode assembly 10 includes an electroactive electrode 20. Electrode 20 includes an exterior connector wire 22, a current distribution member which includes a tab or plate 24 and an optional screen 26. The screen is included only to ensure good contact between the gel matrix 21 and the current distribution member. In one embodiment, electrode 20 would be comprised of silver.

Electrode 20 may have other structures. For example, the electrode described in U.S. Pat. No. 5,147,297 at column 3, lines 44–60, which description is incorporated by reference herein, may be utilized in a practice of this invention. Moreover, as used herein the term "electrode" is not intended to require, but may include, associated drug or electrolyte reservoirs.

Also shown in FIG. 1 is a drug reservoir 18 which, in one practice, comprises a gel or a gel matrix 21. Gel matrix 21 contains the drug or agent species (not shown) which is to be transdermally delivered across the skin barrier. The drug is uniformly dispersed in matrix 21. Drug concentrations in the range of $1\times10^{-4}$M to 1.0M or more can be employed, with drug concentrations in the lower portion of this range being preferred. (A gel matrix such as that described with respect to the drug reservoir of the donor electrode assembly can be utilized in the electrolyte reservoir associated with the counter electrode assembly.)

Any of a number of possible gel matrices may be employed. Agar, polyvinylalcohol, or polyvinylpyrrolidone gels, and the like are well known to one skilled in this art and are advantageously used. If some sort of barrier is employed to define the lower perimeter of reservoir 18, then a non-self supporting, lower-viscosity material may be used. A preferred reservoir material usable for either agent or electrolyte is described in U.S. Pat. No. 5,084,006, which patent is incorporated by reference herein. The reservoir material described in the '006 patent comprises about 10 to 60 weight percent hydrophilic polymer, about 10 to 60 wt. % of a hydrophobic polymer and up to about 50 wt. % of agent or about 60 wt. % electrolyte.

In operation, electrode assembly 10 is placed in contact with a patient's skin and pressed with sufficient firmness so that pressure sensitive adhesive 16 holds drug reservoir 18 in contact therewith by means of housing 12. Electrode assembly 10 is connected to a source of electrical energy, usually a battery, optionally through a current controller. A second electrode assembly (ie, the counter electrode) is then placed in contact with the patient's skin at a site separate from but adjacent to the site of electrode assembly 10 to complete the circuit. Upon activation, transdermal drug or agent delivery occurs.

In accordance with this invention, electrode assembly 10 includes a uniformly or homogeneously dispersed, ion exchange material 19. As shown, ion exchange material 19 is mixed into the hydrophilic gel matrix 21 so that material 19 is uniformly distributed throughout drug reservoir 18.

This feature distinguishes the present invention from prior art electrotransport systems which utilize ion exchange materials. In the prior art, the ion exchange materials are used as a discrete layer or membrane composed substantially entirely of the ion exchange material.

The electrode assembly shown in FIG. 1 also illustrates several of the terms defined above. Ion exchange material 19 is dispersed or commingled with the therapeutic agent in drug reservoir 18. The ion exchange material is dispersed throughout the drug reservoir structure. As such the drug reservoir is a "composite" structure as defined above. Regardless of the terminology, the absence of a discrete, discernable layer, coating, highly concentrated zone or region composed entirely or substantially of ion exchange material, as defined herein, is one of the primary advantages of this invention that, heretofore, has gone unrecognized.

Utilization of a dispersed ion exchange material has several advantages. First, as discussed above, the polarization effect due to Donnan exclusion is greatly reduced or eliminated. Since the ion exchange material is dispersed and does not form a discrete continuous membrane or layer, ion pathways are provided which do not exhibit such polarization effects. Second, an electrode assembly comprising dispersed ion exchange material is easier to manufacture than the same assembly having a discrete or discernable layer or membrane of such material. Generally speaking, the ion exchange material and the drug or agent to be delivered (if the ion exchange material is distributed in the drug reservoir) need only be uniformly mixed or dispersed with each other. Also, due to large surface area and the uniformity of dispersion of the ion exchange material, the ion exchange material provides a uniform distribution of ionic species and therefore a uniformly conductive composite which limits the formation of regions of low ion content (ie, a region having non-uniform concentration of ions of a particular charge which results in increased polarization). Lastly, the ion exchange material is a ready source of ionic species to capture competitive ions or facilitate reactions which generate no competitive ions. This is a distinct advantage over an electrode assembly having a defined or discrete layer or membrane where the species must diffuse to the membrane location before any particular process can occur.

It is within the scope of this invention that the ion exchange material be present in different concentrations in different portions or segments of the electrode assembly or structure. However, the ion exchange material must not be so concentrated in any segment of the structure so as to cause significant polarization due to Donnan exclusion or size selectivity considerations.

In a more preferred practice of this invention, ion exchange material may be dispersed, or distributed proximate to the electroactive substance (alone or in addition to the drug reservoir) as described above. Distribution of the ion exchange material in the electrode has the advantages of (i) optimizing electrotransport drug flux when the ion exchange material is dispersed within the donor electrode assembly; (ii) providing the opportunity for early interaction between the ion exchange material and any competitive species generated by the electrochemically active substance or enhancing the facilitation of reactions which generate no competitive species and (iii) reducing skin irritation which can occur if the ion exchange material is placed in near or direct contact (eg, the material is dispersed in a skin-contact adhesive) with the patient's skin.

In contrast with Parsi U.S. Pat. No. 4,731,049, the present invention does not require the drug to be bound to an ion exchange or ligand affinity medium. In fact, in a preferred practice of this invention, ion exchange material 19 is intentionally selected so as not to bind or absorb a significant amount of the therapeutic agent. If therapeutic agents were bound to the ion exchange material, a reduction in the amount of "free" drug or deliverable species would result. Reduction in the amount of free or deliverable agent or species could reduce overall efficiency of drug delivery. The ion exchange materials described by Parsi inherently have a charge opposite the ion exchange materials described in this invention.

The above discussion has largely assumed that electrode assembly 10 was anodic. It goes without significant additional explanation that an electrode of this invention can be utilized anodically or cathodically. For example, when electrode assembly 10 is cathodic, current distribution member 26 may comprise a silver/silver chloride mesh.

Figure 2:
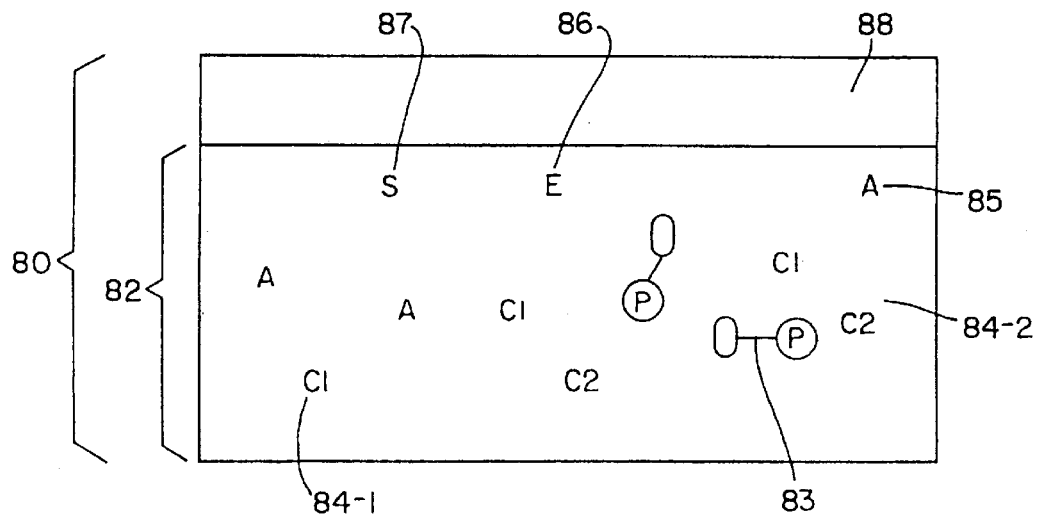
FIG. 2 is a diagrammatic illustration showing an iontophoretic electrode assembly in accordance with the present invention.

FIG. 2 is a sectional view of another active electrode assembly 80 according to the invention. (For purposes of clarity, many details of assembly 80 have been omitted.) In this embodiment, a hydrogel drug reservoir 82 (manufactured as a hydrogel or derived from hydration of substantially dry polymer) contains active agent (A) 85. Active agent 85 will generally have a cationic or anionic form. The dispersed, ion exchange material 83 has charged moieties (P) carrying the same charge as active agent 85. The mobile counter ions C1 and C2 (84-1 and 84-2) of the active agent and the ion exchange material, have an ionic charge opposite that of active agent 85. During iontophoretic operation, electrochemically generated ion E(86) interacts with one or both of the counter ions to form a substantially neutral, insoluble or immobile substance S(87).

Illustrating the above, when A is cationic, eg, protonated hydromorphone, then the ion exchange material is an organic resin with pendent cationic groups (eg, cholestyramine resin sold by Rohm & Haas, Philadelphia, Pa.), the counter ions C1 and C2 are anionic (eg, chloride), the electrode 88 comprises a metal (eg, silver), E(86) is cationic (eg, silver ion) and S(87) is a substantially immobile substance (e.g., silver chloride). Other preferred chloride resins are cross-linked acrylic resins such as Macroprep High Q Support resin sold by Bio-Rod Laboratories, Richmond, Calif.; cross-linked polystyrene resins such as Cholestramine resin, Duolite A-7 resin, Amberlite IRA-68 and IRA-958 resins, all sold by Rohm & Haas, Philadelphia, Pa.; and epichlorohydrin/tetraethylenetriamine resins such as Colestipol sold by the Upjohn Co., Kalamazoo, Mich.

When A is anionic, eg, ketoprofen, then the ion exchange material also is an organic resin with pendent anionic groups (eg, Amberlite IRP-69 sulfonated copolymer of styrene and divinyl benzene commercially available from Rohm & Haas Corporation, Philadelphia, Pa.), the counter ions C1 and C2 are cationic (eg, silver ion), electrode 88 comprises a halide salt (eg, silver chloride), E(86) is an anion (eg, chloride), and S(87) is a substantially immobile substance (eg, silver chloride).

Figure 3:
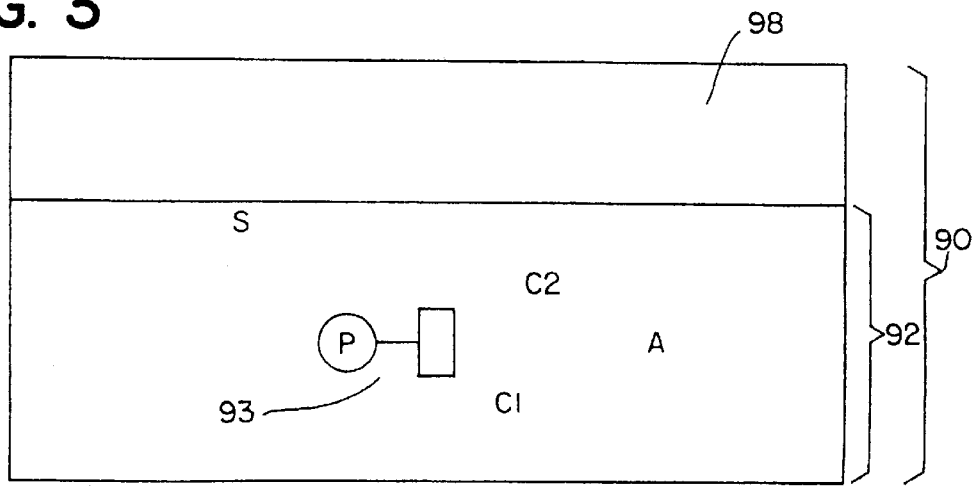
FIG. 3 is a diagrammatic illustration showing a second iontophoretic electrode assembly in accordance with this invention.

FIG. 3 is a sectional view of yet another active electrode assembly 90 according to the invention. For purposes of clarity, many details of assembly 90 have been omitted. In this embodiment, a hydrogel drug reservoir 92 contains active agent (A) which will generally have an anionic or cationic form. The dispersed, ion exchange material 93 has charged moieties (P) carrying the same charge as the active agent. The mobile counter ions (C1 and C2) of the active agent and the ion exchange material have an ionic charge opposite that of the active agent. During iontophoretic operation, the counter ion of the ion exchange material (C2), and optionally the counter ion of the active agent (C1), migrate to electrode 98 and participate in an electrochemical reaction that generates noncompetitive species (S).

More specifically, when the active agent is cationic (eg, protonated hydromorphone), then the ion exchange material component is an organic resin with pendent cationic groups (eg, cholestyramine), the counter ion C2 is anionic (eg, ferrocyanide), the active agent counter ion is anionic (eg, chloride), the electrode 98 comprises an electronically conductive material (eg, conductive carbon), and the noncompetitive species S is anionic (eg, ferricyanide).

When A is anionic (eg, ketoprofen), the ion exchange material is an organic resin with pendent anionic groups (eg, Amberlite IRP-69). The counter ion C2 is a metal cation (eg, $Cu^{2+}$), the active agent counter ion is cationic (eg, $Na^+$), the electrode 98 comprises an electronically conductive material (eg, conductive carbon), and the noncompetitive species S is metallic (eg, copper).

In each of the foregoing examples, the dispersed ion exchange material can also be amphoteric, eg, a resin with both anionic and cationic groups (eg, Bio-Rad AG 501-X8, Bio-Rad Laboratories, Richmond, Calif., USA), provided that substantially all mobile counter ions of the amphoteric polymer C2 are either ionized active agent or other ions that are oppositely charged relative to the ionized active agent. Partially neutralized salts of polyanionic or polycationic resin complexes are specific examples of amphoretic species.

Embodiments for transport of both positive and negatively charged agents, which are contained in separate elements of the electrode assembly may be utilized. In this case, both electrode assemblies will contain active agent and optionally, ion exchange material(s). Embodiments for sequential administration of two similarly charged active agents which are contained in separate electrode assemblies are also possible. In that case, the polarity of the electrode elements may be reversible. The active agent may also be a combination of substances which are to be introduced into the body. In some instances since it may be desired to introduce more than one active agent of the same charge into the body. Therefore, several active agents may be included in the same active electrode element.

The composition of the active or donor electrode assembly of the invention may include ingredients to control or alter their physical properties. Surfactants may be added to a drug reservoir to control the active agent release rate. Humectants may be added to the drug reservoir to control the evaporative loss of water. Preservatives may be added to extend the shelf life of the product. Inert fillers may be added to control the bulk density or to dilute or adjust other properties. Tackifiers may be added to enhance the adhesion of the hydrogel to the skin, electrode, or other structural components of the system. Preferably, the physical properties are adjusted so that the electrode assembly is substantially solid, that is, its consistency is such that the material does not perceptively flow.

Ingredients may also be added to the composition to color it. The coloring of the electrode element may be used as a code to identify the active agent which is admixed in the particular electrode or electrode element.

The polymers used for the polymer of the gel matrix may contain essentially any nonionic synthetic and/or naturally occurring polymeric compounds. A polar nature is preferable when the active agent is polar and/or capable of being ionic since it will enhance the likelihood of agent solubility.

The gel matrix optionally will be water swellable. Synthetic polymers suitable for use in the iontophoretic electrode element are exemplified by: poly(acrylamide), poly(2-hydroxyethyl acrylate), poly(2-hydroxypropyl acrylate), poly(N-vinyl-2-pyrrolidone), poly(n-methylol acrylamide), poly(diacetone acrylamide), poly(2-hydroxylethyl methacrylate), poly(allyl alcohol). Hydroxyl functional condensation polymers (ie, polyesters, polycarbonates, polyurethanes) are also examples of suitable polar synthetic polymers. Polar naturally occurring polymers (or derivatives thereof) suitable for use as the gel matrix are exemplified by: cellulose ethers, methyl cellulose ethers, cellulose and hydroxylated cellulose, methyl cellulose and hydroxylated methyl cellulose, gums such as guar, locust, karaya, xanthan, gelatin, and derivatives thereof. Ionic polymers could be used for the matrix provided that the available counterions are either drug ions or other ions that are oppositely charged relative to the active agent.

Representative ion exchange materials usable in this invention include poly(acrylic acids), poly(acrylic sulfonic acids), poly(acrylic phosphoric acids) and poly(acrylic glycolic acids), polyvinyl amines, polystyrenes, poly epichlorohydrin/tetraethylenetriamines, polymers with pendent amine groups including aromatic amine groups, optionally in combination with tackifiers, which may be included in an adhesive composition. The ion exchange materials could also be primarily inorganic in composition. Silicate and aluminate derivatives, zeolites, ceramic materials with charged surface sites and high surface area, clay materials and polyphosphazenes are possible inorganic ion exchange materials. The present disclosure is likely to suggest many organic and inorganic ion exchange materials usable in this invention to one skilled in this art.

Tackifiers are exemplified by the following materials: polybutene, terpene resins, rosin resin, paraffinic oils, glycols, glycerine, and sorbitol. Humectants which may be included are exemplified by: glycols, glycerine and sorbitol.

Drugs, therapeutic or active agents useful in the present invention include any pharmaceutical compound or chemical that is capable of being ionized or converted to a charged form or is otherwise capable of being delivered by electrotransport. Therapeutic agents, herein, are administered to a host including animals and man for the purpose of obtaining a therapeutic effect. A variety of active agents intended to be introduced into the host may be combined with the matrix. In general, this includes therapeutic agents in all of the major therapeutic areas including, but not limited to, anti-infectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine and ondansetron, antinauseants, antineoplastics, antiparkinsonism drugs, antipruritics, antipsychotics, antipyretics, antispasmodics, including gastrointestinal and urinary anticholinergics, sympathomimetrics, xanthine derivatives, cardiovascular preparations including calcium channel blockers such as nifedipine, beta-blockers, beta-agonists such as dobutamine and ritodrine, antiarrythmics, antihypertensives such as atenolol, ACE inhibitors such as rinitidine, diuretics, vasodilators, including general, coronary, peripheral and cerebral, central nervous system stimulants, cough and cold preparations, decongestants, diagnostics, hormones such as parathyroid hormone, bisphosphoriates, hypnotics, immunosuppressives, muscle relaxants, parasympatholytics, parasympathomimetrics, prostaglandins, proteins, peptides, psychostimulants, sedatives and tranquilizers.

The invention is also useful in the controlled delivery of peptides, polypeptides, proteins and other such species. These substances typically have a molecular weight of at least about 300 daltons, and more typically have a molecular weight of at least about 300 to 40,000 daltons. Specific examples of peptides and proteins in this size range include, without limitation, LHRH, LHRH analogs such as buserelin, gonadorelin, napharelin and leuprolide, GHRH, GHRF, insulin, insultropin, heparin, calcitonin, octreotide, endorphin, TRH, NT-36 (chemical name: N-[[(s)-4-oxo-2-azetidinyl]carbonyl]-L-histidyl-L-prolinamide), lipercin, pituitary hormones (eg, HGH, HMG, HCG, desmopressin acetate, etc), follicle luteoids, αANF, growth factors such as growth factor releasing factor (GFRF), βMSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirulog, hyaluronidase, interferon, interleukin-1, interleukin-2, mentropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, bradykinin antagonists, CD4, ceredase, CSI's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonists analogs, alpha-1 antitrypsin (recombinant), and TGF-beta.

Additional agents include pilocarpine nitrate, lidocaine hydrochloride, hydrocortisone derivatives, sodium salicylate, acetic acid, fluoride anion, lithium, antibiotics such as penicillin and cephalosporin and dexamethasone sodium phosphate, hydromorphone, diazepam salts, antihypertensive agents, bronchodilator agents, peptide hormone and regulatory agents and proteins.

The electrode assemblies formed using these agents are generally used as the active or donor electrodes.

The following examples are illustrative of the processes and materials used to obtain the electrode compositions of the invention. These examples should not be utilized to restrict the scope of this invention.

EXAMPLE 1

In this example a narcotic analgesic, in the form of a hydrochloride salt, is delivered via electrotransport from a device having a silver anodic donor electrode. Silver anodic electrodes are desirable from the standpoints that (1) silver is electrochemically oxidizable (ie, $Ag \rightarrow Ag^+ + e^-$) and hence substantially prevents water hydrolysis (ie, $H_2O \rightarrow 2H^+ + \frac{1}{2}O_2 + 2e^-$), and (2) silver is relatively non-toxic and well tolerated by the human body. Unfortunately, silver cations generated by the oxidation of the silver anode undesirably compete with a cationic drug for electrotransport delivery. Further problems with delivery of silver cations into the skin is the tendency of silver to discolor the skin and for silver ions to degrade some active agents and/or matrix materials. In order to prevent silver migration during cationic drug delivery, the prior art has taught the desirability of formulating the drug as a chloride salt. Thus, the chloride counter ions of the drug react with the electrochemically generated silver ions to form AgCl which is substantially water insoluble and hence precipitates from solution. Unfortunately, under conditions of high current densities, high drug fluxes and/or long term delivery we have discovered that formulating the drug as a chloride salt does not always provide a sufficient quantity of chloride ions to prevent silver ions from migrating into the reservoir containing the active agent. Under these conditions it is necessary to provide a supplementary source of chloride ions, preferably without introducing a potentially competing source of cations, to the anodic electrode.

To this end, cholestyramine resin was added to a hydrogel matrix which also contained a hydrochloride drug salt. Cholestyramine resin (CST) is a strongly basic ion-exchange material in the chloride form, consisting of styrene-divinylbenzene copolymer with quaternary ammonium functional groups. The chloride content of CST ranges from 13.0% to 17.0% on a dry weight basis. CST, when added to an aqueous liquid, forms a high molecular weight, substantially immobile cation and a mobile chloride counter ion. In operation, the silver anode oxidizes to produce $Ag^+$ions. $Ag^+$ions react with the CST's counter ion, ie, the chloride ions, to produce AgCl which is substantially water insoluble and hence precipitates out of aqueous solutions. Since the CST macromolecule is quite large, the CST cation cannot migrate and thereby compete with delivery of the drug cations.

To evaluate the use of CST for prevention of silver migration, the following experiment was performed. Hydrogel matrices containing CST and a hydrochloride salt of a narcotic analgesic drug were prepared. Each hydrogel matrix had a cross sectional area of 2 $cm^2$ and was composed of 4.8% CST, 1.5% drug salt, 3.6% hydroxypropyl methylcellulose, 5.4% polyvinyl alcohol, and water. The chloride content of each hydrogel matrix was 2.2 milliamp hours (mAh). That is, the chloride content was sufficient to react with 2.2 mAh of electrochemically generated silver ion (eg, 22 hours at 0.1 mA). Of the total 2.2 mAh of chloride in each hydrogel matrix, 0.4 mAh of chloride was from the drug counterion and 1.8 mAh of chloride was from the CST. Additional chloride is gained from skin during operation of the device.

Nine hydrogel matrices were each placed in contact with a microporous polycarbonate membrane used as a model for human skin. A 0.1M $NaNO_3$ receptor solution contacted the opposite surface of the membrane. A nitrate salt was chosen for the receptor solution, rather than saline, in order to ensure that the receptor solution contributed essentially no chloride ions into the system being tested. A silver foil anode was placed against each hydrogel matrix and a silver chloride cathode was placed in each receptor solution. Electrotransport of the analgesic drug across the microporous membrane was achieved with a constant current of 0.1 mA applied for up to 32 hours. Drug flux was determined by periodic sampling of the receptor solutions. The silver content of the hydrogel matrices was determined after 16, 24, and 32 hours of electrotransport.

A steady state drug flux of approximately 60 $\mu g/cm^2 \cdot h$ was observed. Table 1 compares the amount of silver detected in each hydrogel matrix to the amount of silver ion electrochemically generated by a current of 0.1 mA over that period of time. As indicated in Table 1, CST prevented any silver ions from migrating into the drug reservoir matrix for at least the first 16 hours of operation. After 24 and 32 hours of operation, small amounts of silver were detected in the hydrogel matrices, presumably because the available chloride from the CST starts to become depleted after about 20 hrs of operation. Thus, the CST successfully minimized the amount of silver ion which migrated into the hydrogel matrices. Those skilled in the art will appreciate that loading more CST in the anodic electrode system will permit longer periods of operation without any silver migration.

TABLE 1

| Cell No. | Time of Current Application (h) | Amount of Ag$^+$ Generated ($\mu$g) | Amount of Ag$^+$ Detected in Hydrogel Matrix ($\mu$g) |
|---|---|---|---|
| 1 | 16 | 6450 | 0 |
| 2 | 16 | 6450 | 0 |
| 3 | 16 | 6450 | 0 |
| 4 | 24 | 9670 | 104 |
| 5 | 24 | 9670 | 124 |
| 6 | 24 | 9670 | 293 |
| 7 | 32 | 12890 | 362 |
| 8 | 32 | 12890 | 870 |
| 9 | 32 | 12890 | 1673 |

EXAMPLE 2

This example illustrates the utilization of a generic class of dispersed ion exchange material, ie, chloride-rich ionomers derived from poly-amino-functional acrylates, poly-aromatic amines, or poly-amino-functional saccharides. In addition to minimizing silver migration, the chloride-rich ionomer preferably has minimal impact on drug transport out of a donor reservoir matrix and into the body. Table 2 compares the amount of the same narcotic analgesic delivered through human epidermis over a period of 24 hours at a current density of 100 $\mu$A/cm$^2$ from silver anodic electrode/hydrogel matrix formulations similar to that described in Example 1, except the matrices each contained 2.4 mAh of chloride provided by one of the following chloride-rich ionomers:

poly-2-trimethylammonium ethylacrylate chloride (TMAEAC);

poly-2-trimethylammonium ethylmethacrylate chloride (TMAEMC);

poly-N-trimethylammonium propylmethacrylamide chloride (MAPTAC);

poly-Diethylaminoethyl-Dextran (DEAED); or cholestyramine (CST).

Visual observations of the hydrogel matrices were made immediately following the 24 hour delivery. If the matrix contained a whitish precipitate which turned grey upon exposure to light, silver migration into the drug reservoir was indicated. As indicated in Table 2, cholestyramine permitted the highest drug flux while still preventing silver migration into the drug reservoir matrix. Hence, cholestyramine is the preferred form of chloride-rich ionomer for delivery of this particular drug since it prevented silver migration yet still permitted the highest level of drug flux.

TABLE 2

| Chloride-Rich Ionomer | Drug Delivered in 24 hrs (mg) | Silver Migration Observed |
|---|---|---|
| TMAEAC | 0.22 | No |
| DEAED | 0.24 | No |
| TMAEMC | 0.60 | No |

TABLE 2-continued

| Chloride-Rich Ionomer | Drug Delivered in 24 hrs (mg) | Silver Migration Observed |
|---|---|---|
| MAPTAC | 0.60 | No |
| CST | 1.60 | No |
| None | 2.10 | Yes |

In addition to the materials listed in Table 2, the following chloride-rich ionomers listed in Table 3 may also be used in an anodic reservoir to limit silver ion migration from a silver anode:

TABLE 3

| Resin | Polymer Type | Functional Group | Chloride Ion Capacity (meq/g) Wet | Chloride Ion Capacity (meq/g) Dry | Water Soluble Extractable Fraction (mg/g dry resin) |
|---|---|---|---|---|---|
| Cholestyramine | Styrene/ divinylbenzene | RN(CH$_3$)$_3$Cl | 3.9 | 4.4 | 7.7 |
| Bio-Rad AG 3-X4 | Styrene/ divinylbenzene | RH(CH$_3$)$_3$Cl | 2.6 | 6.1 | 0.0 |
| Duolite A-7 | Phenolic/ amine | R$_2$NHCl | 1.6 | 2.9 | 16.5 |
| Amberlite IRA-68 | Acrylic/ divinylbenzene | RN(CH$_3$)$_3$Cl | 2.0 | 3.3 | 4.2 |
| Amberlite IRA-958 | Acrylic/ divinylbenzene | RN(CH$_3$)$_3$Cl | 1.3 | 1.9 | 0.2 |
| Macroprep High Q | GMA/ EGDMA/amine | RN(CH$_3$)$_3$Cl | 0.6 | 0.8 | 0.0 |
| Colestipol | ECH/amine | R$_3$N | 2.5 | 2.5 | 0.0 |

In addition to the use of chloride-rich ionomers in the drug reservoir of an anodic electrode assembly, the ionomer may also be placed in other components within the anodic electrode assembly, such as the anodic electrode itself or in an in-line skin contact adhesive layer position between the anodic drug reservoir and the skin. The following two examples describe compositions in which cholestyramine is placed in an anodic electrode and an anodic skin contact adhesive layer, respectively.

EXAMPLE 3

A polymer based, silver-containing anodic donor electrode, having a reduced tendency to exhibit silver ion migration when silver ions are generated by the electrochemical oxidation of the silver in the electrode, was made as follows. First, 25.0 g of a pre-blended polyisobutylene (PIB) matrix (50 wt % polyisobutylene VISTANEX grade LM-MS having a molecular weight of about 35,000 daltons and 50 wt % of polyisobutylene VISTANEX grade MM L-100 having a molecular weight of 1.2 million daltons, both sold by Exxon Chemical Corporation, Houston, Tex.) were added to a 50 cm$^3$ Brabender mixer (Brabender Instruments, Hackensack, N.J.) over a one minute period. The mixer was initially at room temperature and set at a mixing speed of 12 rpm. Next, 129 g of silver powder (8–12 $\mu$m particle size) and 11.5 g cholestyramine resin (Duolite AP-143/1083 particle size 150 $\mu$m or less, sold by Rohm & Haas, Philadelphia, Pa.) were pre-mixed in a beaker and then added to the Brabender mixer over a period of 30 minutes. The ingredients were mixed for an additional 25 minutes.

The mixture was then removed from the mixer, sandwiched between two release liners, each having a thickness of 0.08 mm (3 mils), and fed through a pair of counter rotating calendar rolls heated to about 90° C. and rotating at a speed of 15 cm/min (0.5 ft/min). The calendar rolls were set with a gap of about 0.3 mm (12 mils). The resulting polymer based anodic electrode film had a thickness of 0.15 mm (6 mils).

The ion conducting properties of this composite anode formulation can be optionally enhanced by the addition of hydrophilic ingredients, such as polyvinyl alcohol (PVA), polyvinyl pyrrolidone (PVP), starch, or other nonionic polymers. The electron conducting properties of the composite anode formulation can be optionally enhanced by the addition of electron-conducting ingredients, such as carbon black, carbon fiber, graphite, and metallic powders, flakes, or fibers composed of gold, stainless steel, titanium, tungsten, or the like.

EXAMPLE 4

An ion-conducting skin contact adhesive film adapted to adhere an anodic donor electrode assembly containing electrochemically oxidizable silver to the skin of a patient, which adhesive film limits the amount of oxidized silver ions migrating therethrough, was made as follows. First, 36.4 g of a pre-blended polyisobutylene (PIB) matrix (80 wt % polyisobutylene VISTANEX grade LM-MS having a molecular weight of 35,000 daltons and 20 wt % of polyisobutylene VISTANEX grade MM L-100 having a molecular weight of 1.2 million daltons, both sold by Exxon Chemical Corporation, Houston, Tex.) were added to a 60 cm$^3$ Haake mixer (Haake, Inc., Paramus, N.J.) over a one minute period. The mixer was initially at room temperature and set at a mixing speed of 20 rpm. Next, 11.5 g cholestyramine resin (Duolite AP-143/1083, particle size less than 150 μm, sold by Rohm & Haas Company, Philadelphia, Pa.) were added to the Haake mixer over a period of 10 minutes. The ingredients were mixed at 25 rpm for an additional minutes.

The mixture was then removed from the mixer, sandwiched between two release liners, one having a thickness of 0.08 mm (3 mils) and the other having a thickness of 0.03 mm (1 mil), and fed several times through a pair of counter rotating calendar rolls heated to about 100° C. and rotating at a speed of 20 cm/min (0.7 ft/min). On the last pass through the calendar rolls, the rolls were set with a gap of 0.2 mm (7 mils). The resulting adhesive film was tacky to the touch and had a thickness of 0.06 mm (2.5 mils).

The ion-conducting properties of this CST/PIB composite adhesive can be optionally enhanced by the addition of hydrophilic ingredients such as polyvinyl alcohol, polyvinyl pyrrolidone, starch or other nonionic polymers.

EXAMPLE 5

This experiment compares the amount of narcotic analgesic drug delivered through a microporous polycarbonate membrane in 24 hours at 50 μA/cm$^2$ from silver anodic electrode/hydrogel matrices of the type described in Example 1, containing 2.4 mAh of a chloride rich ionomer (poly-TMAEMC) in three different forms. One hydrogel matrix contained a crosslinked form of poly-TMAEMC in a thin zone adjacent the silver anode. Another hydrogel matrix contained a granular form of crosslinked poly-TMAEMC distributed throughout the hydrogel matrix. A third hydrogel matrix contained a solution of poly-TMAEMC (uncrosslinked) distributed throughout the hydrogel matrix. Visual observations of silver migration were made as in Example 2. Table 4 lists the narcotic analgesic flux observed from each type of hydrogel matrix relative to that observed using a hydrogel matrix without TMAEMC. The "layered" and "granular" distributions of insoluble poly-TMAEMC exhibited similar drug fluxes which were much larger than the drug flux observed for the soluble poly-TMAEMC.

TABLE 4

| Form of TMAEMC | Drug Flux (% of Control*) | Silver Migration Observed |
|---|---|---|
| Soluble; uncrosslinked | 13 | No |
| Insoluble, crosslinked in granular form | 76 | No |
| Insoluble, crosslinked in the form of a distinct layer | 88 | No |
| None | 100 | Yes |

*Control had no poly-TMAEMC in hydrogel.

EXAMPLE 6

In this Example an anodic composite intercalation electrode is used to deliver a cationic drug by electrotransport. The composite electrode is comprised of a intercalation-type material which is preferably in the form of a powder, fibers or flakes, mixed with a suitable polymer binder such as polyisobutylene. Intercalation materials for use in an anodic electrode should be oxidizable and are preferably stable in the presence of air and water when in their reduced state. Upon oxidation, the intercalation material of the composite anode will preferably incorporate anions from the surrounding medium (eg, Cl$^-$) into its structure to maintain local charge neutrality. An example of this type of intercalation material is graphite intercalated with a metal chloride, such as FeCl$_2$ or organic polymers such as polypyrroles, polyanilines, and polymethoxythiophene. Other intercalation materials will expel cations (eg, Ag$^+$) from their structure when oxidized. Examples of this type of intercalation material are transition metal oxides such as tungstates, molybdates, and vanadates, or organic polymers such as a copolymer of methylpyrrolylium and styrene sulfonate.

As in Example 3, the ion-conducting and/or the electron-conducting properties of this composite anode can be optionally enhanced by the addition of a hydrophilic ion-conducting material (eg, polyvinyl alcohol) or an electron-conducting material (eg, carbon black). In both these cases an ion exchange material would be included to provide ions which are intercalated into the composite anode or interact with a de-intercalated ion to form a substantially immobile substance.

EXAMPLE 7

In this Example, a cathodic composite intercalation electrode is used to deliver an anionic drug by electrotransport. This composite electrode is comprised of an intercalation-type material which is preferably in the form of a powder, fibers or flakes, mixed with a suitable polymeric binder such as polyisobutylene. Intercalation materials for use in a cathodic electrode should be reducible and are preferably stable in the presence of air and water when in their oxidized state. Upon reduction, the intercalation material of the composite cathode will preferably incorporate cations from the surrounding medium (eg, Na$^+$) into its structure to maintain local charge neutrality. Examples of this type of intercalation material are transition metal oxides such as tungstates, molybdates, and vanadates, or organic polymers such as a copolymer of methylpyrrolylium and styrene sulfonate. In this example, the ion exchange material will provide a source of ions to be intercalated into the cathode. Other intercalation materials will expel anions (eg, $Cl^-$) from their structure when reduced. An example of this type of intercalation material is graphite intercalated with a metal chloride, such $FeCl_3$, or organic polymers such as polypyrroles, polyanilines, and polymethoxythiophene. In this example, the ion exchange material provides silver ions to react with the chloride ions produced.

As in Example 3, the ion-conducting and/or the electron-conducting properties of this composite cathode can be optionally enhanced by the addition of a hydrophilic ion-conducting material (eg, polyvinyl alcohol) or an electron-conducting material (eg, carbon black).

EXAMPLE 8

In this Example, a source of silver ions (ie, a silver 2-acrylamido-2-methylpropane sulfonate (AMPS) polymer material) is added to the cathodic drug reservoir of a device having a metallic cathodic electrode (eg, stainless steel, copper or silver). During normal operation of the device, the silver ions migrate to the metallic cathode and are reduced to silver metal. Of course, the polymeric AMPS anions remain in solution, however, because of their high molecular weight they are relatively immobile and therefore present minimal electrotransport competition.

In a preferred embodiment, the cathode is composed of silver chloride. As the silver ion is reduced and deposited on the silver chloride cathode during operation, silver ion is depleted in the vicinity of the cathode. If the migration of silver to the cathode is too slow, then the cathodic potential will increase to a level where reduction of silver chloride will occur. Chloride ions will then migrate into the hydrogel and react with the silver ions from the silver-AMPS to form insoluble silver chloride and substantially immobile poly-AMPS anions.

The silver AMPS material is prepared by adding silver carbonate commercially available from Aldrich Co. of Milwaukee, Wis., to a 15% aqueous solution of acid AMPS, a non-cross linked 2-acrylamido-2-methyl propane sulfonic acid polymer available under the trade name ACCELOMER 100 from Joats, Inc. (Champlin, Minn.). The acid AMPS is converted to the silver salt by reacting with the silver carbonate, according to the following reaction: $Ag_2CO_3+ 2H\text{-}AMPS \rightarrow 2Ag\text{-}AMPS+CO_2+H_2O$. The reaction mixture is stirred until the $CO_2$ evolution ceases to be detectable by visual inspection.

A polyvinyl alcohol (PVA) hydrogel is mixed with the silver AMPS and an aqueous solution of sodium diclofenac (ie, diclofenac anions) is imbibed into the PVA gel. The silver chloride cathode is placed on the diclofenac-containing PVA gel to form a cathodic electrode/drug reservoir assembly.

EXAMPLE 9

In this Example, a cathodic composite electrode is used to deliver an anionic drug by electrotransport, the anionic drug being present in the form of an aqueous solution of a drug salt. The composite electrode is comprised of a stainless steel powder mixed with polyisobutylene (PIB). Since water has a lower reduction potential than stainless steel, water rather than the stainless steel is electrochemically reduced in order for current to pass from the stainless steel composite electrode to the aqueous drug solution in the drug reservoir. In general, when using an aqueous drug solution in a cathodic reservoir, water is hydrolyzed in accordance with the following reaction: $H_2O+e^- \rightarrow \frac{1}{2}H_2+OH^-$. Unfortunately, reduction of water produces hydroxyl ions which compete with the drug anions for electrotransport delivery from the cathodic electrode assembly. In order to prevent this competition, an ion exchange material, eg, a high molecular weight acid such as polyacrylic acid or an ion exchange material having a fixed negative charge and mobile hydronium ions is mixed into the composite cathode with the stainless steel powder and PIB. Examples of cation exchange resins with mobile hydronium ions include strong acid (sulfonic acid) cation-exchange resins such as IRP-64 and IRP-69, both sold by Rohm & Haas, Philadelphia, Pa. Hydronium ions from the high molecular weight acid or cation ion exchange material react with the electrochemically generated hydroxyl ions to produce neutral water. In the case of the acidic cation-exchange resin, the counter ion of the anionic drug being delivered (eg, a metal cation such as $Na^+$, $K^+$, $Ca^{+2}$, or $Mg^{+2}$) is exchanged for the hydronium ions of the resin.

Another source of "mobile ionic species" results from efflux of endogenous cations (eg, sodium ions) from the body into the cathodic drug reservoir. The released hydronium ions react with the electrochemically generated hydroxyl ions to produce neutral water. In this manner, competition for electrotransport delivery between the anionic drug and electrochemically generated hydroxyl ions is substantially avoided since the high molecular weight anionic resin/acid has little or no mobility even under the influence of an electric field.

The ion-conducting and/or the electron-conducting properties of this composite cathode can be optionally enhanced by the addition of a hydrophilic material (eg, PVA) or an electron-conducting material (eg, carbon black).

EXAMPLE 10

In this Example, a catalytic anodic composite electrode is used to deliver a cationic drug by electrotransport, which cationic drug is in the form of an aqueous solution of a drug salt. The composite electrode is comprised of a polyisobutylene matrix loaded with stainless steel powder and a high molecular weight hydroxide resin. Although stainless steel powder is used in this formulation, other catalytic materials such as carbon, platinum and gold in powder, flake or fiber form can be substituted for the stainless steel.

The composite electrode can be prepared by pre-blending a polyisobutylene (PIB) matrix (50 wt % polyisolbutylene VISTANEX grade LM-MS having a molecular weight of 35,000 daltons and 50 wt % of polyisobutylene VISTANEX grade MM L-100 having a molecular weight of 1.2 million daltons, both sold by Exxon Chemical Corporation, Houston, Tex.) in a 60 $cm^3$ Hakke mixer (Haake, Inc., Paramus, N.J.) over a one minute period. The mixer is initially at room temperature and set at a mixing speed of 12 rpm. Next, stainless steel powder (8–12 $\mu$m particle size) and a high molecular weight hydroxide resin (AG 1-x 8 sold by BioRad Laboratories of Richmond, Calif.) are preblended in a beaker and are then added to the Haake mixer over a period of 10 minutes. The ingredients are mixed at 25 rpm for an additional 25 minutes.

Since water has a lower oxidation potential than stainless steel, water rather than the stainless steel is electrochemically oxidized in order for current to pass from the composite stainless steel electrode to the aqueous drug solution in the drug reservoir. In general, when using an aqueous drug solution in an anodic reservoir, water is hydrolyzed in accordance with the following reaction: $H_2O \rightarrow 2H^+ + \frac{1}{2}O_2 + 2e^-$. Unfortunately, oxidation of water produces hydronium ions which compete with the drug cations for electrotransport delivery from the anodic electrode assembly. However, the high molecular weight hydroxide or resin (eg, BioRad's AG 1-X8) added to the composite electrode prevents this competition. During operation, this hydroxide resin releases hydroxyl ions which react with the electrochemically generated hydronium ions to produce neutral water.

The ion-conducting and/or the electron-conducting properties of the composite anode can be optionally enhanced by the addition of a hydrophilic material (eg, PVA) or an electron-conducting material (eg, carbon black).

We claim:

1. An electrotransport device having one or more ion conducting regions comprising:
a donor electrode assembly including an electrode and a donor reservoir containing an active agent,
a counter electrode assembly including an electrode,
means for maintaining the device in ion transmitting relationship with a body surface or membrane;
a source of electrical power adapted to be electrically connected to the donor and counter electrode assemblies; and
particulate means for substantially immobilizing competitive ions located in at least one of the ion conducting regions, wherein said competitive ions are generated within at least one of the electrode assemblies during operation of the device and said particulate means comprises an ion exchange material distributed in at least one of said electrodes in order to form a composite electrode structure comprising an electronically conductive composition and an ion exchange material, said ion exchange material comprising a mobile ionic species and a substantially immobile ionic species, the mobile ionic species being interactive with said competitive ions so that said competitive ions are rendered substantially less mobile or less responsive to electromotive force generated by the device.

2. An electrotransport device having one or more ion conducting regions comprising:
a donor electrode assembly including an electrode and a donor reservoir containing an active agent,
a counter electrode assembly including an electrode;
means for maintaining the device in ion transmitting relationship with a body surface or membrane;
a source of electrical power adapted to be electrically connected to the donor and counter electrode assemblies; and
particulate means located in at least one of the ion conducting regions, said particulate means comprising an ion exchange material comprising a mobile ionic species and a substantially immobile ionic species, the mobile ionic species being capable of being incorporated into at least one of said electrodes.

3. The device of claims 1 or 2 further including a hydrogel in the donor reservoir, wherein the hydrogel contains an amount of said particulate means.

4. The device of claims 1 or 2 wherein the means for maintaining the device in ion transmitting relationship with the body surface or membrane is provided with an amount of said particulate means.

5. The device of claims 1 or 2 wherein the donor electrode is provided with an amount of said particulate means.

6. The device of claims 1 wherein the donor electrode is anodic comprising silver that oxidizes producing competitive ions which react with mobile ionic species comprising chloride ions.

7. The device of claim 1 wherein the particulate means for immobilizing competitive ions is a member selected from the group consisting of styrene/divinylbenzene chloride, silver 2-acrylamido-2-methylpropane sulfonate, polydiethylaminoethyl-dextran, poly-N-trimethylammonium propylmethacrylamide chloride, poly-2-trimethylammonium ethylmethacrylate chloride, poly-2-trimethylammonium ethylacrylate chloride, phenolic/amine chloride, acrylic/divinylbenzene chloride, GMA/EGDMA/amine chloride, and poly-epichlorohydrin/tetraethylenetriamine.

8. The device of claim 1 wherein the particulate means for immobilizing competitive ions is a member selected from the group consisting of poly-amino functional acrylates, poly-amino functional saccharides, high molecular weight hydroxide resins, sulfonic acid cation exchange resins, poly (acrylic acid), poly(acrylic sulfonic acid), poly(acrylic phosphoric acid), poly(acrylic glycolic acid), polyvinyl amine, ECH/amine chloride, polystyrene resins, a polymer with pendant aromatic amine groups, silicates, aluminates, zeolites, ceramics, clays and polyphosphazenes.

9. The device of claims 1 or 2 wherein the form of the particulate means is a member selected from the group consisting of a particle, grain, pellet, colloid, micelle, powder, fiber and flake.

10. The device of claim 9 wherein the size of the particulate means is about 0.1 to 1200 $\mu$.

11. The device of claim 9 wherein the size of the particulate means is about 600–1200 $\mu$.

12. The device of claim 9 wherein the size of the particulate means is about 100–600 $\mu$.

13. The device of claim 9 wherein the size of the particulate means is about 5–150 $\mu$.

14. The device of claims 1 or 2 wherein the donor electrode assembly includes an electrode comprising silver chloride.

15. The device of claims 1 or 2 comprising $1 \times 10^{-4}$ to 1.0 molar active agent in the donor reservoir, wherein the agent is fentanyl.

16. The device of claims 1 or 2 wherein the particulate means has a water soluble fraction less than about 0.1 wt. %.

17. The device of claims 1 or 2 wherein the particulate means has a water soluble fraction less than about 0.001 wt. %.

18. The device of claim 2 wherein the ion exchange material is distributed within at least one of said electrodes in order to form a composite electrode structure comprising an electronically conductive composition and an ion exchange material.

19. The device of claim 18 wherein the mobile ionic species is capable of being incorporated into the electronically conductive composition.

20. The device of claim 1 or 19 wherein the electronically conductive composition comprises an intercalation material.

21. The device of claim 20 wherein the intercalation material is selected from the group consisting of graphite intercalated with metal chlorides, transition metal oxides, inorganic materials, and organic polymers.

22. The device of claim 21 wherein the intercalation material comprises a material selected from the group consisting of graphite intercalated with $FeCl_2$ or $FeCl_3$; polypyrrole; polyaniline; polymethoxythiophene; partially oxidized sodium tungstate; partially oxidized sodium molybdate; partially oxidized sodium vanadate; and a copolymer of methylpyrrolylium and styrene sulfonate.

23. The device of claim 2 wherein at least one of said electrodes comprises an intercalation material and the mobile ionic species is capable of participating in an intercalation reaction.

24. The device of claim 23 wherein the intercalation material is selected from the group consisting of graphite intercalated with metal chlorides, transition metal oxides, inorganic materials, and organic polymers.

25. The device of claim 24 wherein the intercalation material comprises a material selected from the group consisting of graphite intercalated with $FeCl_2$ or $FeCl_3$; polypyrrole; polyaniline; polymethoxythiophene; partially oxidized sodium tungstate; partially oxidized sodium molybdate; partially oxidized sodium vanadate; and a copolymer of methylpyrrolylium and styrene sulfonate.

26. The devices of claim 1 or 20 wherein the electronically conductive composition further comprises a conductive filler selected from the group consisting of carbon black, carbon fiber, graphite, metallic powders, metallic flakes, and metallic fibers.

27. The device of claim 1 or 2 at least one of said electrode assemblies further comprises a hydrophilic ion conducting material selected from the group consisting of polyvinyl alcohol, polyvinyl pyrrolidone, and starch.

28. The device of claim 1 or 2 wherein the drug is selected from peptides, polypeptides and proteins.

29. The device of claim 28 wherein the drug has a molecular weight of at least 300 Daltons.

30. The device of claim 28 wherein the drug is selected from the group consisting of LHRH, LHRH analogues, GHRH, GHRF, mentropins, insulin, pituitary hormones, and growth factors.

* * * * *